(12) United States Patent
Norgren et al.

(10) Patent No.: US 8,658,814 B2
(45) Date of Patent: Feb. 25, 2014

(54) CHEMICAL AND METHOD FOR CHELATING METAL IONS INCLUDED IN WATER AND SEPARATING/RECOVERING OF FORMED CHELATE

(75) Inventors: Hans Magnus Norgren, Matfors (SE); Nils Fredrik Andersson, Sundsvall (SE); Ida Helena Högberg, Sundsvall (SE); Kjell Håkan Edlund, Sundsvall (SE); Sten Erik Hedenström, Stöde (SE)

(73) Assignee: Chemseq International AB, Sundsvall (SE)

( * ) Notice: Subject to any disclaimer, the term of this patent is extended or adjusted under 35 U.S.C. 154(b) by 453 days.

(21) Appl. No.: 12/997,713

(22) PCT Filed: Jun. 10, 2009

(86) PCT No.: PCT/SE2009/000293
§ 371 (c)(1),
(2), (4) Date: Feb. 1, 2011

(87) PCT Pub. No.: WO2009/151366
PCT Pub. Date: Dec. 17, 2009

(65) Prior Publication Data
US 2011/0124898 A1 May 26, 2011

(30) Foreign Application Priority Data

Jun. 13, 2008 (SE) ...................................... 0801392

(51) Int. Cl.
*C07F 13/00* (2006.01)
*C07C 229/00* (2006.01)
(52) U.S. Cl.
USPC ........................................... 556/45; 562/565
(58) Field of Classification Search
USPC ........................................... 556/45; 562/565
See application file for complete search history.

(56) References Cited

U.S. PATENT DOCUMENTS 4,741,831 A    5/1988  Grinstead

FOREIGN PATENT DOCUMENTS

WO    98/14657 A1    4/1998
WO    98/17857 A1    4/1998

OTHER PUBLICATIONS

Gaku Izumi, et al; "Foamy Complex Formation for Removing and Recovering of Heavy Metal Ions in Dilute Solution with N-Monodecanoyl Diethylenetriamine", Bulletin of The Chemical Society of Japan, vol. 49 (7), 1727-1731, 1976.
International Search Report; PCT/SE2009/000293 (2009).

*Primary Examiner* — Porfirio Nazario Gonzalez
(74) *Attorney, Agent, or Firm* — Harness, Dickey & Pierce, P.L.C.

(57) ABSTRACT

The present invention relates to a chemical for chelation of metal ions, which are at least bivalent, contained in water and/or water enclosed objects and separation/recovering of formed chelate; the structural formula of which is formula (I) where R in at least one of the positions shown is comprised of a group in the form of a straight or branched hydrocarbon chain having from 9 to 20 carbon atoms, and where appropriate 1-2 hetero atoms, and which is missing in other position(s); and where X in shown positions is in a group in the form of —COOH or its salt; and wherein the chemical can be a racemate, a mixture of enantiomers, or pure enantiomers or where R is missing in all four positions shown X in at least one position is —COOR, —CONHR or —CH$_2$OR or —COR or —CH$_2$OCOR or —CH$_2$OCONHR; and where X in the remaining positions shown is comprised of a group in the form of —COOH or its salt; and wherein the chemical can be a racemate, a mixture of enantiomers, or pure enantiomers.

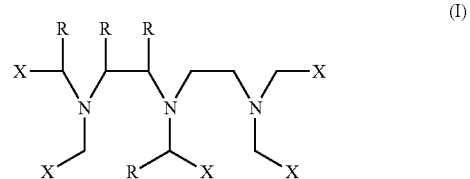

24 Claims, 3 Drawing Sheets

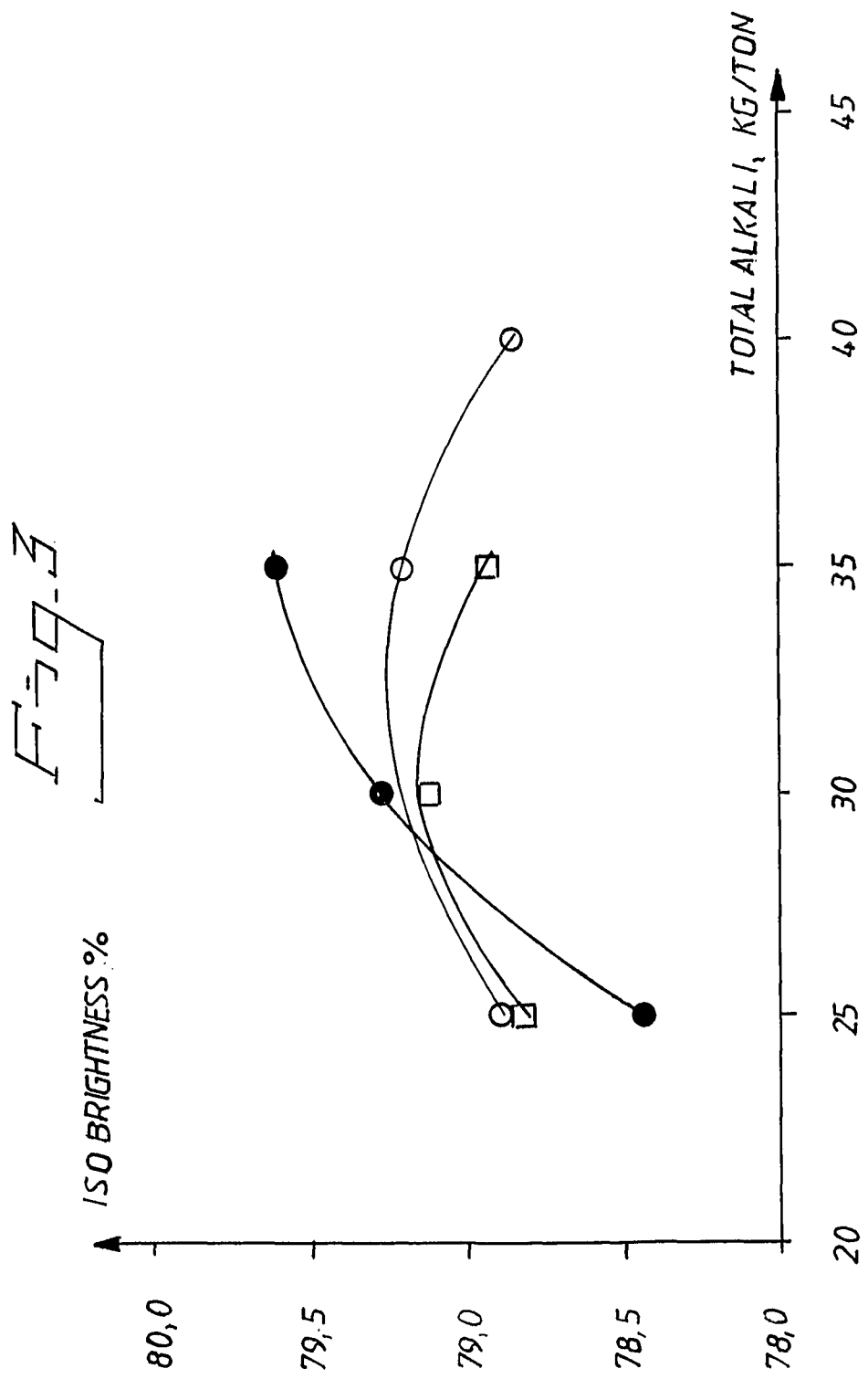

CHEMICAL AND METHOD FOR CHELATING METAL IONS INCLUDED IN WATER AND SEPARATING/RECOVERING OF FORMED CHELATE

TECHNICAL FIELD

The present invention relates to a certain type of sequestering agents and their use.

Sequestering agents have been used for a long time within a very large number of technical fields.

One important area of use is in bleaching of cellulose pulp with for example different types of peroxides and most common hydrogen peroxide. Lignocellulosic material, such as wood, which is the starting material in the production of cellulosic pulp, contains a large number of metals, which to a substantial degree is maintained in the material, also when it is converted into cellulose pulp, such as chemical cellulose pulp as well as mechanical cellulose pulp. Examples of undesired metal ions are manganese ions, copper ions and iron ions. These ions catalyze the degradation of peroxide, such as hydrogen peroxide, and are therefore undesired. Also the water which has to be used in the manufacture of cellulose pulp requested by the market (for the production of paper, rayon, cellophane etc) including in the bleaching treatment, contains said metal ions in varying concentrations. Normally cellulose pulp (usually containing at least 70% water) is treated with sequestering agents in a separate step and the complexes formed are normally removed from the cellulose pulp immediately before for example a peroxide is added to the cellulose pulp. Also in several other positions of cellulose pulp manufacturing processes it is conventional to use sequestering agents.

Sequestering agents are also used in many other industrial connections where materials has to be purified, such as before varnishing, painting, galvanizing and other coating. Also in the manufacturing industry for electronics and textiles sequestering agents are used. In all cases the metal complexes (chelates) formed are washed away from the respective materials and are transferred to an outlet. Sequestering agents are used in cleaning also when it comes to consumer products in the form of for example washing-up detergents, detergents, shampoos and toothpastes. All these agents will end up in the sewage system after use.

A further field of application for the chemical, that is the sequestering agents, according to the invention is purification of soil, sediments, leachate, etc. These objects should be relieved from environmentally harmful heavy metals, such as cadmium, cobalt, chromium, mercury, manganese, copper, zinc etc. According to the invention the heavy metals are not only taken away from the objects but the chelates are also taken care of resulting in that the heavy metals can be taken care of and be deposited and possibly be rendered harmless.

Technical Standpoint

For a long time there has been a large number of sequestering agents on the market. Common sequestering agents are EDTA (ethylenediaminetetraacetic acid), DTPA (diethylenetriaminepentaacetic acid) and NTA (nitrilotriacetic acid). A disadvantage with these sequestering agents is that they are neither separable nor recoverable.

More recently very sophisticated, molecularly bulky sequestering agents, to some extent similar to the chemical claimed here, have been developed. All of these are already in advance bonded to a metal ion and it is the complex (chelate) as such that is used for medical purposes, either as the curing medicament or most common as a contrast agent.

One example of the above can be found in the international (PCT) patent application WO 2005/048987.

There are two independent claims in this patent application and they are worded as follows; "A liposome containing a hydrophobic chelate compound as a membrane component."

"An MRI contrast medium, which comprises a liposome according to any one of claims 1 to 3."

In page 11 in the patent application the structural formula for such a complex is shown, which is repeated below.

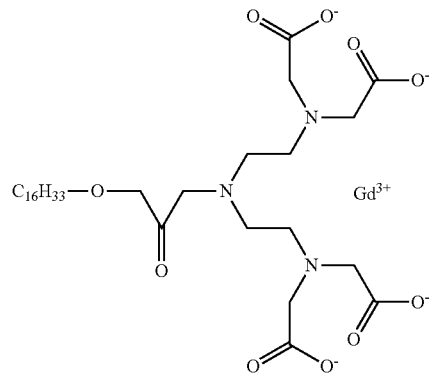

The metal ion to which the sequestering agents is bonded in this case is gadolinium $3^+$ and apparently it is the metal ion that is important from the aspect of the contrast agent. Regarding the sequestering agent as such it is a demand that it binds said metal ion in an indissolvable manner.

There are also articles in magazines discussing chelates of MRI-type. One example of this is "Gadolinium DTPA-Monoamide Complexes Incorporated into Mixed Micelles as Possible MRI Contrast Agents" by Tatjana N. Parac-Vogt et al., Eur. J. Inorg. Chem., 2004, p. 3538-3543. Herein they start with the following teaching:

"MRI (Magnetic resonance imaging) contrast agents are routinely used in medicine because they provide reliable results that assist in the rapid clinical interpretation of MRI images. Most of the commonly used contrast agents achieve their effect by enhancing the relaxation rate of water protons in tissues. In general, contrast agents consist of a paramagnetic metal centre, typically gadolinium (III), which must be complexed to a strong chelating ligand, since the free metal ions are toxic at the concentrations needed for diagnosis. Water-soluble anionic $[Gd(DTPA)(H_2O)]^{2-}$ was the first contrast agent approved for use in humans and is currently in routine use as a clinical magnetic resonance imaging agent under the name Magnevist® {Schering, Berlin, Germany). This complex contains one inner-sphere water molecule[1-4] that exchanges rapidly with bulk water[5], providing an efficient relaxation of the surrounding water protons. However, $[Gd(DTPA)(H_2O)]^{2-}$ is a non-specific contrast agent since its hydrophilicity results in an efficient enhancement of contrast only through its preferential distribution in the bloodstream. In recent years, contrast agents with improved characteristics, such as increased efficiency and organ specificity, have been sought."

(Our underlinings)

As is evident they are not completely satisfied with the first generation of complexes based on the chemical DTPA as such, but instead they aim at an enhanced complex based on an enhanced sequestering agent.

On page 3539 in the article they describe among others as number III the following sequestering agent:

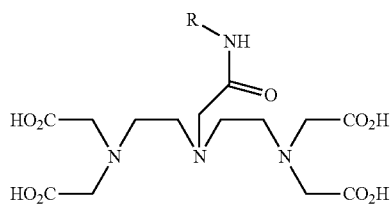

In the article an abstract is presented with the following wording:

"Four monoamides derivatives of Gd-DTPA with alkyl chains consisting of 12, 14, 16 or 18 carbon atoms were synthesized. The gadolinium (III) complexes with chain lengths of 14, 16 or 18 carbon atoms were efficiently incorporated into mixed micelles whereas the complex with a chain length of 12 carbon atoms was not incorporated into a micellar structure. The size distribution of the micelles was measured by photon correlation spectroscopy. The mean sizes of the micelles for all the complexes lay within a narrow range, typically between 11 and 20 nm. The NMRD curves of the gadolinium (III) DTPA-monoamide complexes incorporated into mixed micelles display higher relaxivity values than the commercially available Gd-DTPA contrast agent. Moreover, micelles with gadolinium DTPA-monoamide complexes showed higher relaxivities than micelles containing the corresponding gadolinium DTPA-bis(amide) complexes, most likely because of more efficient exchange of the coordinated water molecule."

From this it is clear that in order to have an optimal result of a complex in this connection (as well as in other connections) the sequestering agents has to be tailored. Here a chemical works, which regarding the hydrocarbon chain=R has 14, 16 and 18 carbon atoms, but not the chemical with 12 carbon atoms in the hydrocarbon chain.

DESCRIPTION OF THE INVENTION

Technical Problem

The sequestering agents today used as a matter of routine form complex (chelate) with different metal ions and these complexes will finally end up normally in some kind of recipient, where they are stored for a very long time, since the complexes as well as the sequestering agent as such (this is normally added in excess) are hardly degradable. From an environmental aspect there is a need of a sequestering agent, which as such and in combination with metals, that is as complexes, can be separated from for example the recipient and as an alternative is recovered, possibly with a repeated use. As in many cases a cycle process is the optimum.

The Solution

The present invention fulfills the above mentioned needs or, described in another way, solves the above mentioned problems, and consists of a chemical for chelating (sequestering) of metal ions, which are at least bivalent, comprised in water containing and/or water enclosed objects and for separating/recovering of formed chelates, characterized in that its structural formula is

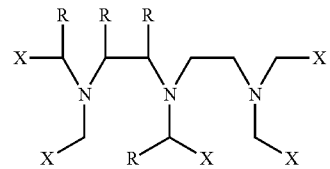

wherein R in at least one of the positions shown is comprised of a group in the form of a straight or branched hydrocarbon chain having from 9 to 20 carbon atoms and eventually 1-2 heteroatoms and which is missing in other position(s) and wherein X in at least four of the positions shown is a group in the form of —COOH or the salt thereof and which in the case of four groups is missing in one position and wherein the chemical can be a racemate or a mixture in different proportions or pure enantiomers, or where R is missing in all four positions shown X in at least one position is —COOR or —CONHR or —CH$_2$OR or —COR or —CH$_2$OCOR or CH$_2$OCONHR and where X in the remaining of the positions shown is comprised of a group of —COOH or its salt and where the chemical can be a racemate or a mixture in different proportions or pure enantiomers. With heteroatoms is per definition meant all other atoms but carbon and hydrogen. In this case it is preferably a question of sulphur, oxygen, nitrogen and possibly an atom within the group halogens.

As is defined above R is a group in the form of a straight or branched hydrocarbon chain having from 9 to 20 carbon atoms and in some cases 1-2 heteroatoms. With this is meant, which is obvious for anyone, that the group does not have to contain any heteroatom. It is even preferred that heteroatoms are excluded. In the case the group contains one or two heteroatoms it is not impossible that one or two carbon atoms in the chain is (are) exchanged for the heteroatom(s). However, it is most suitable that this or those is (are) placed in one of the ends of the hydrocarbon chain as an addition to the same. For example it is suitable to place the heteroatom(s) between the carbon atom of interest in the structural formula and the hydrocarbon chain. In case it is a question of two atoms it may be two atoms of the same kind or two different atoms.

When the group R exists as a solitaire in the chemical it is preferably placed in at least one of the three positions being shown to the left and at the top in the structural formula shown. Presence of one or two such groups is preferred and in the case with one group it is preferably placed in position two counted from the left in the structural formula.

The length of R, that is the hydrocarbon chain, is decided by the field of use for the chemical, that is the sequestering agent.

If for example leachate shall be purified, that is if one wishes to take care of heavy metals existing in leachate and harmful for the environment, the number of carbon atoms should be many, for example fifteen to twenty. The same goes for other objects similar to leachate, that is where the most dominating constituent in the object is water.

If the water constituent of the object is not completely dominating, as in the above described case, but instead it is a question of for example cellulose pulp fibers, which shall be freed from at least bivalent metal ions, the length of the hydrocarbon chain should be shorter, for example containing ten to fourteen carbon atoms. In certain cases a number of twelve carbon atoms is optimum. If you use a too long hydrocarbon chain in such cases it has been found to be hard to get the chemical as a whole, that is with its considerable extension, in certain objects to move into and through these for the uptake of undesired, at least bivalent metals.

In case the group R is missing as solitaire in the structural formula and is comprised in the modified "X" according to the above, three of the above listed and possible groups are preferred and they are —CONHR, —CH$_2$OR and —COR. The most preferred group is —CONHR.

One chemical proven to be suitable for use is 4-dodecyl-3, 6,9-tri(carboxymethyl)-3,6,9-triazaundecane diacid or its salt. This chemical has the following structural formula

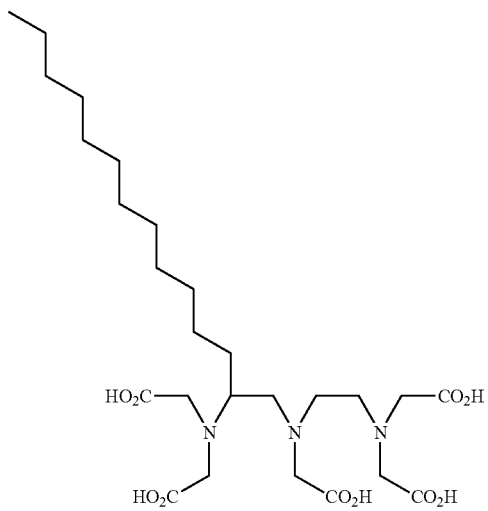

The invention also comprises a chemical for chelating (complex binding) of metal ions, which are at least bivalent, comprised in water containing and/or water enclosed objects and for separating/recovering of formed chelates, characterized in that its structural formula is

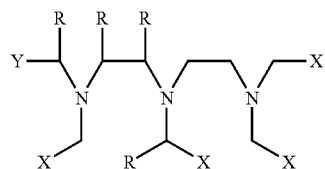

where R in at least one of the positions shown is comprised of a group in the form of a straight or branched hydrocarbon chain having from 9 to 20 carbon atoms and where appropriate 1-2 heteroatoms and which are missing in other position(s) and where X in the shown positions is a group in the form of —COOH or its salt and where Y is —COOR or —CONHR, or —CH$_2$OR or —COR or —CH$_2$OCOR or —CH$_2$OCONHR and where the chemical can be a racemate or a mixture in different proportions or pure enantiomers.

One chemical of the above described type, which has proven to be suitable for use for the described purpose is 4-decyl-3,6,9-tri(carboxymethyl)-3,6,9-triazaundecanediacid-1-carboxy-11-N-decylamide or its salt. This chemical has the following structural formula

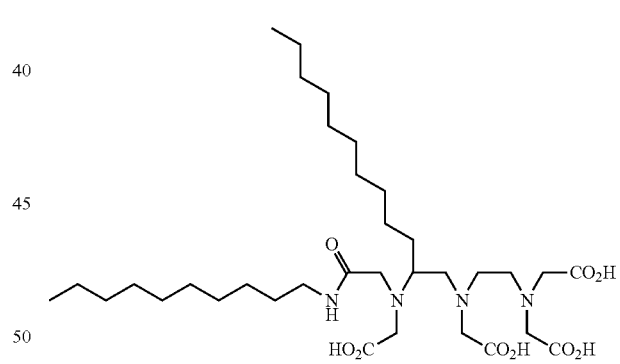

A third chemical having proven to be suitable for use for the described purpose is 3,6,9-tri(carboxymethyl)-3,6,9-triazaundecanediacid-1-carboxy-11-N-dodecylamide or its salt. This chemical has the following structural formula

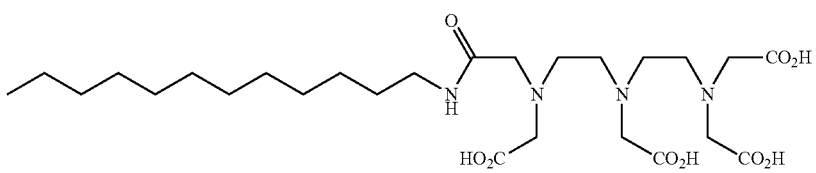

This chemical falls under both of the main groups of chemicals having been shown and described above.

Of course also a number of other chemical individuals can be used besides the three above specified and falling under said main groups be used as sequestering agents within the described technical field.

The invention also comprises a method for taking care of or recovering sequestering agents (chelating agents) which have been brought to react with metal ions, which are at least bivalent, comprised in water containing and/or water enclosed objects, comprising that the complex (chelate) formed being comprised in a liquid phase is separated from the object relieved of metal and is brought to a flotation plant, wherein gas, for example air, bubbles stream upwards in the liquid phase together with becoming and/or existing solid substances, including the complex, in the form of a foam to the liquid surface, which foam is removed from the liquid surface and is taken care of, characterized in that the sequestering agent added to react with at least bivalent metal ions is a chemical having the following structural formula

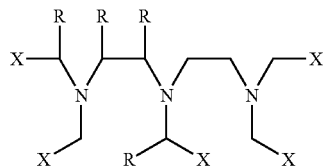

where R in at least one of the positions shown is comprised of a group in the form of a straight or branched hydrocarbon chain having from 9 to 20 carbon atoms and where appropriate 1-2 heteroatoms and which is missing in other position(s) and where X in at least four of the positions shown is a group in the form of —COOH or its salt and which in a case with four groups is missing in one position and where the chemical may be a racemate or a mixture in different proportions or pure enantiomers, or when R is missing in all four positions shown X in at least one position is comprised of —COOR or —CONHR or —CH$_2$OR or —COR or —CH$_2$OCOR or —CH$_2$OCONHR and where X in the remaining of the positions shown is comprised of a group in the form of —COOH or its salt and where the chemical can be a racemate or a mixture in different proportions or pure enantiomers.

In the case where the object is cellulose pulp fibers which, for example in a step before a bleaching step, is treated with sequestering agents for taking care of the appropriate metal ions of the cellulose pulp fibers and the cellulose pulp fibers in a subsequent washing is separated from a liquid phase comprising formed complexes, fatty acids and resinous acids released from the cellulose pulp fibers are used in order to facilitate the formation of said foam.

In the case wherein the object does not release the fatty acids and/or resinous acids at least one surfactant is added to the liquid phase to facilitate the formation of said foam.

The foam is removed/separated from the flotation vessel(s) and is taken care of in original or collapsed form and is carried away for combustion or dumping.

In the alternative case according to the invention in which the sequestering agent shall be recovered acid is added to the collected foam so that its pH-value is reduced to somewhere within the interval 0-3, leading to that protons (H$^+$) take the place of the metal ion in the complex and in that resinous acids and fatty acids or the surfactant is precipitated together with the metal ions in a liquid phase formed by the foam followed by a separation of these substances and that in the liquid phase prevalent ion exchanged sequestering agent is extracted, with an organic solvent, whereupon the solvent phase is brought to meet a water phase with a pH-value at or close to neutral (pH=7), leading to that the sequestering agent is transferred into liquid phase and can be used again to release the object from the appropriate metal ion.

The acid added is a mineral acid or a carbonic acid. The organic solvent can be any of the substances pentane, hexane, heptane or ethers or possibly any mixture of these substances. The above described separated substances, however not the sequestering agent, is brought to combustion or dumping. The solvent separated from the liquid phase is used again for extraction of ion exchanged sequestering agent.

Advantages

The sequestering agents used in practice today are neither separable nor recoverable.

The sequestering agent according to the invention is just that and this opens for important environmental progress and advantages. On one hand it will be the end of or at least a great reduction of dumping of sequestering agents (depending on overdoses) as well as formed complexes (chelates) to different recipients. Moreover, with the sequestering agent according to the invention it is possible to take care of old environmental sins. There is both land and sediment that is contaminated with heavy metals and in many cases one does not want to go in and touch these materials because of the threat that it might be even worse from an environmental aspect. With the sequestering agent according to the invention it is possible to once and for all relieve these objects from undesired heavy metals. Further different water flows can be finally purified, such as leachate flows, from undesired heavy metals.

Even if the manufacturing cost for the sequestering agent according to the invention is higher than the manufacturing cost for traditional sequestering agents, the first mentioned sequestering agent will be cheaper in the long run (besides environmental savings), since the sequestering agent can be used repeatedly, that is time after time.

With the properties of the sequestering agent according to the invention in the form of separability and recoverability further advantages follow, which are not explicitly discussed here in order to save space.

DESCRIPTION OF DRAWINGS

In FIG. 3 is shown bleaching results in the form of brightness of the cellulose pulp, which before the bleaching has been treated with sequestering agents, one conventional and two according to the invention.

BEST EMBODIMENT

In the following is described with reference to FIGS. 1 and 2, preferred embodiments of the method according to the invention and finally a number of examples are reported.

Figure 1:
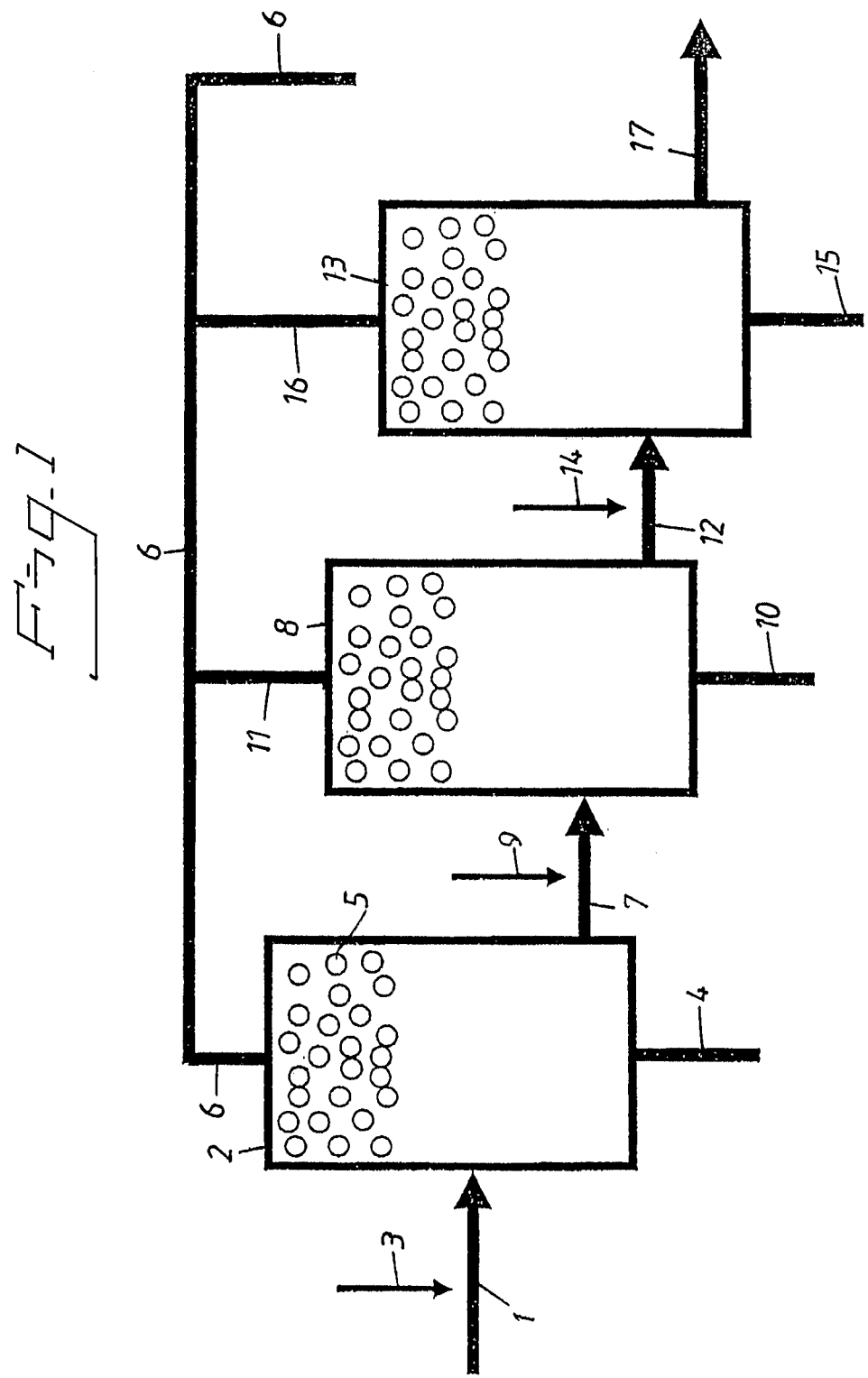
In FIG. 1 is shown how to complex bind heavy metals in leachate and separate the complexes from the leachate.

In FIG. 1 is shown how leachate is transported to the flotation vessel 2 through conduit 1. Through the conduit 3 a chemical is added to the leachate, that is a sequestering agent, according to the invention. In this case a sequestering agent is to be used comprising a long hydrocarbon chain (see what has been stated above about R and R being comprised in a modified X) and the number of carbon atoms in the hydrocarbon chain should lie within the interval fifteen to twenty and preferably at or around twenty.

In order to succeed with a subsequent flotation it might be necessary to add at least one surfactant, together with the sequestering agent or separate from that to the leachate, for example of the type alkylsulphates, alkylsulphonates, alkylcarboxylates, alkylethoxylates and compounds of a similar character.

At the bottom of the flotation vessel 2 air is added through conduit 4, which in the form of gas bubbles 5 flows upwards in the vessel 2.

In the independent method claim is stated the alternative "becoming . . . solid substances, including the complex" and the following is what is intended with said wording.

The gas bubbles 5 are normally spherical and in their periphery or casing is a very thin layer containing the complex together with water in a very small amount. The complex is probably oriented so that the hydrocarbon chains points out from the layer while the metal ions and the remaining part of the complex is inside the very thin layer.

When all these gas bubbles 5 arrive at the top of the vessel 2 they exist in the form of a foam, which is scraped off from the top surface part of the leachate column and this foam is removed through the main conduit 6.

Since it is difficult for the added sequestering agent to momentarily capture all heavy metal ions, which exist in the added leachate, that is the leachate flow that is to be purified, the above described procedure is repeated.

The leachate partly relieved from heavy metals is transported through the conduit 7 to a second flotation vessel 8. Through conduit 9 is added further sequestering agents and possibly also a surfactant. Air is supplied through the conduit 10 and the foam formed is transported through the conduit 11 to the main conduit 6. In a third step leachate is led through the conduit 12 to the flotation vessel 13. Chemicals are added through the conduit 14 and air through the conduit 15. The foam is removed through the conduit 16 to be introduced into the main conduit 6.

Leachate completely relieved from heavy metals is removed from the conduit 17 and formed foam is transported further to dumping or preferably to destruction by combustion. Ashes obtained at the combustion in for example steam boilers already contain large amounts of heavy metals, for which reason the addition of heavy metals coming from the leachate does not imply any problems. The sequestering agent is degraded at the combustion down to for example inert nitrogen, water and carbon dioxide.

Figure 2:
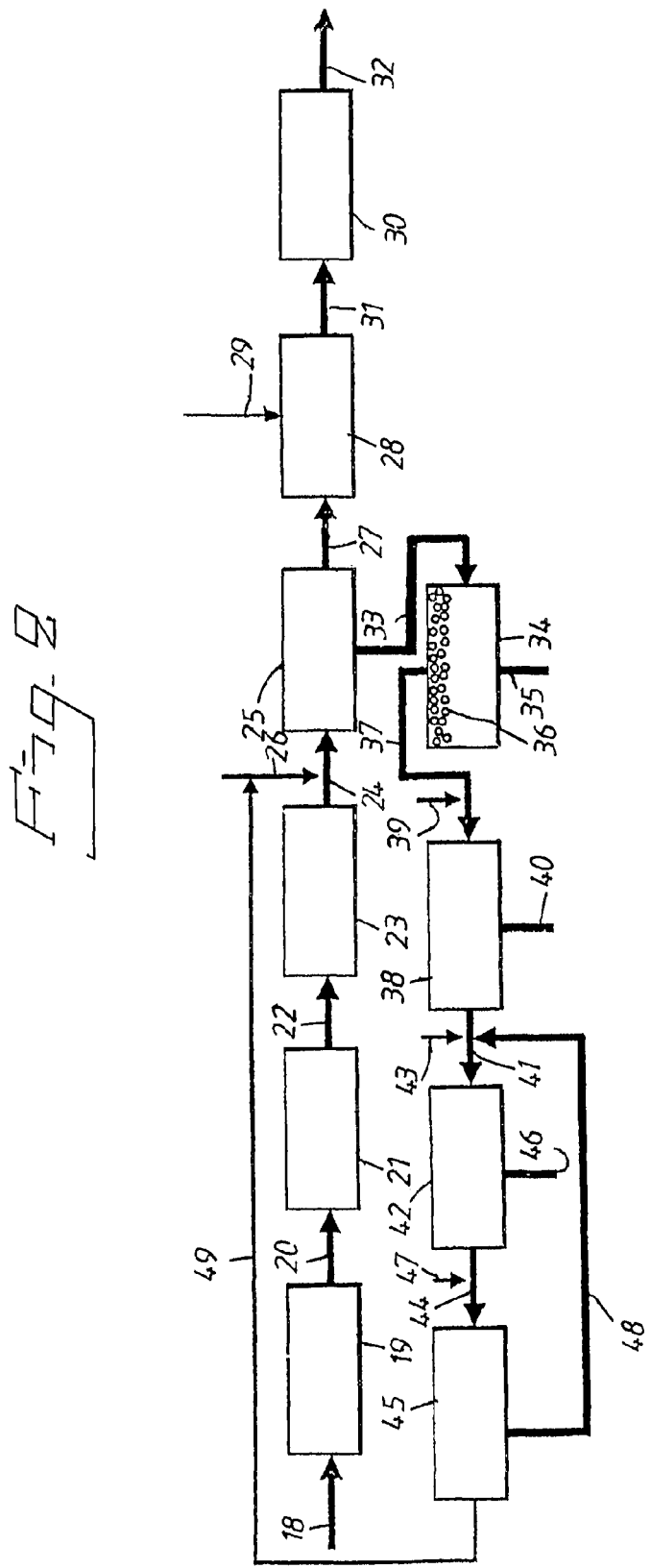
In FIG. 2 is shown how to relieve cellulose pulp with the aid of sequestering agents from metals degrading bleaching agent (peroxide) and recover the sequestering agent for repeated use.

In FIG. 2 is shown bleaching of a mechanical cellulose pulp with hydrogen peroxide, wherein sequestering agents according to the invention are added to the cellulose pulp for capturing of undesired metals (including manganese ions) in the cellulose pulp before the bleaching step and for recovery of sequestering agents, which are rejected from the cellulose pulp manufacturing process in the form of chelates (complexes).

Wood chips are input through the conduit 18 to the refiner 19 wherein the wood chips are converted to cellulose pulp. This is transported through the conduit 20 to a screening department 21. Subsequently the screened and/or hydrocyclone purified cellulose pulp is fed through the conduit 22 to a washing step 23. From this step the cellulose pulp is led through the conduit 24 to a press (or wash press) 25. On the way to the press 25 a sequestering agent is added to the cellulose pulp according to the invention through the conduit 26.

Cellulose pulp with a high pulp concentration is led through the conduit 27 (for example with the aid of a screw conveyor) to a chemical mixer 28, to which is added bleaching chemicals through the conduit 29 in the form of hydrogen peroxide and sodium hydroxide and possibly some further chemicals, such as water glass ($Na_2SiO_3$). Thereafter the cellulose pulp is fed into the bleaching tower 30 through the conduit 31. After a bleaching time of the order of magnitude hours the bleached cellulose pulp is further led through the conduit 32 to a washing step (not shown in the figure).

Later on the main part of the method according to the invention (additional sequestering agents through the conduit 26 has already been described) will be described.

The liquid resulting in the press 25, that is liquid pressed out from the cellulose pulp suspension with its content of chelate (complex) is led through the conduit 33 to a flotation vessel 34. Through the conduit 35 air is added to the flotation vessel 34, and air flows upwards in the vessel in the form of bubbles 36. As has been described earlier the air bubbles will bring the complexes to the top of the flotation vessel 34 in the form of a foam, which foam is removed/separated from the top surface of the liquid column and is transported through the conduit 37 to the acid treatment vessel 38. The purified, that is flotated pressed material, is fed out of the flotation vessel 34 for a possible completing treatment (not shown in the figure).

Since the cellulose pulp fibers give away fatty acids and resinous acids to the pressate it is not absolutely necessary to add any aiding flocculating agent, for example in the form of a surfactant. However it cannot be excluded that an aiding flocculating agent has to be added. This might be dependent on which single chemical (sequestering agent) according to the invention that is accessible, that is how high its separation capability is, and how hard it is to flocculate the liquid to be purified or relieved from complexes.

Through the conduit 39 an acid is added to the possibly collapsed foam, such as a mineral acid or carbonic acid ($CO_2$). Enough acid is added to make the pH-value of the formed liquid to fall within the interval 0-3. As a result of the acidification protons ($H^+$) take the place of the metal ion in the complex and further the complexes are separated in the vessel 38 from fatty acids and resinous acids and the metal ions recovered from the cellulose pulp plus possible auxiliary flocculent. The last mentioned substances are removed from the vessel 38 through the conduit 40, while the complexes are led through the conduit 41 to the extraction vessel 42. Any known and for this purpose suitable extraction agent, for example heptane, is added through the conduit 43. The sequestering agent molecules, with its proton instead of metal ion, are converted from the water phase to the solvent phase and this is led through conduit 44 to the dwell vessel 45. The water phase with its content of diverse chemicals is ejected from the system through the conduit 46.

To the solvent phase containing the sequestering agent is through conduit 47 added an alkaline aqueous solution of such a strength and in such an amount that the pH-value in the water phase becomes at least 7. Hereby the sequestering agent will go from the solvent phase over to the aqueous phase. These two phases are separated from each other and the solvent phase is returned into the system through the conduit 48 and is input in position 43. The aqueous phase containing the recovered sequestering agent is returned into the system through the conduit 49 and is input in position 26.

Since the solvent as well as the sequestering agent is recovered the conduits 26 and 43 symbolize only addition of fresh, non-used chemicals. The fresh addition of these chemicals is, as is obvious for any one, very limited in amounts and correspond to the spillage occurring in the system for the respective chemical. Concerning the pH-value of the sequestering agent it shall, as has been stated earlier, be at least 7. How far above 7 one wishes to go in the separate case is decided partly based on how stable the sequestering agent is at different pH-values.

Example 1

A thermomechanical pulp (TMP) manufactured from spruce was bleached in the laboratory, which pulp before the bleaching has been relieved from the main part of the manganese content by the addition of three different sequestering agents forming manganese containing chelates, which by washing thoroughly were removed from the cellulose pulp before the bleaching treatment.

The cellulose pulp was removed directly after the refiner in a TMP-plant and its dry solids content was determined with the aid of "Mettler Toledo HR 73 Halogen Moisture Analyzer". 70 g bone-dry cellulose pulp was then slushed in 1.4 l cold distilled water with the aid of a slusher of model "Lorentzon & Wettre App. 03, type 8-3, no. 723". The cellulose pulp with a concentration of 4.8 percent by weight was filtered on a Büchner funnel and the filtrate was returned to be filtered again. Thereafter the cellulose pulp was slushed in 1.4 l distilled water at a temperature of 55° C. The pulp suspension was left to stand for 1 h and was then filtered two times according to the same process being described above. Again the cellulose pulp was slushed in 1.4 l distilled water at a temperature of 55° C. To three different portions of the cellulose pulp suspension was added one sequestering agent, two according to the invention and one traditional and more specifically DTPA. The added amount of sequestering agent was 0.17 mmol, corresponding to a molar ratio of manganese/sequestering agent of 1:1.3 at an anticipated manganese content in the cellulose pulp of 100 ppm. The pH was measured in the pulp suspension and it amounted to 6.2 and the cellulose pulp suspension was allowed to stand, i.e. the sequestering agent was allowed to work for a time of 60 min. Thereafter the formed chelate was removed from the cellulose pulp by filtration of the same in the above described way.

The manganese content of the cellulose pulp was determined, on one hand, on non-treated pulp, and on the other hand on the portions having been treated with the respective sequestering agents. This analysis was performed in the following way. 10 g of bone-dry cellulose pulp was transferred to a platinum crucible. The sample was heated to 300° C. and was stored at that temperature for a time of 2 h. During the treatment the sample was carbonized. Thereafter the sample was calcined at 575° C. for a time of 3 h. 5 ml 8 M nitric acid was added and the sample was concentrated to an amount of about 2.5 ml by evaporation on a heating plate. A few drops of hydrogen peroxide (30 percent by weight concentration) were added and the sample was heated until the hydrogen peroxide had decomposed into hydrogen and oxygen, that is until the bubbling ceased. After cooling to room temperature the sample solution was transferred to a calibrated measuring cylinder of a volume of 25 ml and the sample solution was diluted up to the mark with water of quality "Milli-Q". The sample solution was analyzed in view of among other things manganese content with the aid of an analyze instrument of the type ICP-AES of the brand "Thermo Jarrel Ash, Irish Advantage Instrument".

The three sequestering agents used in the experiments were:

1=DTPA=conventional sequestering agent=○

2=4-dodecyl-3,6,9-tri(carboxymethyl)-3,6,9-triazaundecane diacid=sequestering agent according to the invention=□

3=3,6,9-tri(carboxymethyl)-3,6,9-triazaundecanediacid-1-carboxy-11-N-decylamide=sequestering agent according to the invention=●

It appeared that the starting cellulose pulp had a manganese content in mg/kg of 36, while all portions of the cellulose pulp treated with sequestering agents and being relieved from the chelates, had a manganese content within the interval 1.5-2 mg/kg.

The three portions of the cellulose pulp being relieved from their manganese content through the described sequestering agent treatment were bleached with hydrogen peroxide according to the following.

The cellulose pulp in the form of a suspension was pressed to a dry solids content of 37%. The dry solids content was determined as has been described above. The amount of different liquids, that is the water content of the cellulose pulp, the sodium hydroxide solution, the hydrogen peroxide solution and the water glass solution were calculated and in order to get the pulp concentration mentioned below at the bleaching a suitable amount of distilled water was added. The concentrations stated below are given in percent by weight of bone-dry pulp.

Pulp consistency=30%

Hydrogen peroxide addition=4%

Water glass addition=2.4% (gives an approximate addition of 12% NaOH of total alkali)

Sodium hydroxide addition=varying

To a bleaching mixer with a temperature of 70° C. was added cellulose pulp and water and mixing was performed for 5 min. The sodium hydroxide solution and the water glass solution were poured in a beaker and the hydrogen peroxide solution in another beaker, where after the content in these beakers were mixed quickly and thereafter added through the spray nozzle into the bleaching mixer. The chemical containing liquid was sprayed over the cellulose pulp suspension and was mixed for a time of 7 min. The cellulose pulp suspension supplied with chemicals was transferred to a bleaching bag, which was welded up.

The bleaching bag was then placed in a water bath with a temperature of 70° C. and was kept there during 2 h. Thereafter the bleaching bag was taken up from the water bath and was cooled during 10 min in cold water. 8 g (26.66 g, 30 percentage) bone-dry cellulose pulp was taken from the bag and was mixed with 0.5 l distilled water for the manufacture of brightness sheets, as is described below.

Brightness sheets with a grammage of 40 g/m$^2$ were manufactured according to the following.

The cellulose pulp sample was mixed with distilled water and was diluted with this up to a volume of 2 l. pH was measured and was adjusted to 5.0±0.3 with sodium hydroxide or sulphuric acid. 0.5 l of the described pulp suspension was transferred to a sheet form with wire cloth and filter paper. The water was allowed to drain, where after vacuum was activated and the last water was aspirated. The paper sheet form was removed and placed between two filter papers. Another three sheets were manufactured in the same way and were then piled according to the following:

Press plate
Two dry blotting papers
Filter paper
The paper sheet, that is the sheet for determining the brightness
Filter paper
Two dry blotting papers
and the above repeated.

This pile was pressed at a pressure of 0.1 MPa during 1 min. The press plates and the blotting papers were removed and the paper sheets were placed on drying plates in a conditioned room (25° C., 50% relative humidity) overnight. The brightness of the paper sheets was measured the next day with the brightness meter Elrepho SE 071/070R (ISO 2469).

In FIG. 3 the measured brightness is plotted versus the total amount of sodium hydroxide added at the bleaching for the three cellulose pulps, which were treated with sequestering agents.

The symbols of the graphs has been defined earlier, but are repeated here in short form;
1=conventional sequestering agent=○
2=sequestering agent according to the invention=□
3=sequestering agent according to the invention=●

The brightness of the paper sheets manufactured from cellulose pulp treated with sequestering agent 1, that is a conventional sequestering agent, corresponds to a large extent with the brightness of the paper sheets manufactured from cellulose pulp, which has been treated with sequestering agent 2 according to the invention. From these two graphs you may get the impression that a total addition of sodium hydroxide, calculated in kg/ton cellulose pulp, of a little bit more than 30 kg is optimal from a brightness point of view.

The graph describing the brightness of paper sheets manufactured from cellulose pulp having been treated with sequestering agent 3 according to the invention has a different form. At low concentrations of total alkali the brightness falls somewhat compared with the zero sample, that is sequestering agent 1, while it is the total opposite at high levels total alkali, that is the brightness is higher than for the zero sample.

The most important fact that can be understood from these experiments is that the ability of the sequestering agents according to the invention to bind for example manganese ions is comparable with the ability of the traditional sequestering agents to bind manganese ions.

Example 2

In order to investigate the separability of a sequestering agent according to the invention the following laboratory experiment was made.

The sequestering agent that was investigated was the sequestering agent, which in the preceding example 1 was given the reference 2 and is symbolized with □.

This sequestering agent and 21 mg manganese in the form of manganese sulphate were mixed in a molar ratio of 1.2:1 in 100 ml distilled water. The pH-value of the solution was adjusted to 7.0 with a 0.1 M sodium hydroxide solution. The solution was carefully stirred during the time of 4 h. Thereafter the solution was transferred to a laboratory flotation cell of the type "Voith Delta 25". 20.9 l distilled water was added and the stirring switched on. The temperature of the solution was increased during a certain time up to 70° C. At the beginning 20 ml of the solution was taken for determination of the manganese content. A flocculating agent of the type EKA RF 4283 was added to the solution and more exactly 0.38 g when the temperature of the solution was 25° C. and 0.23 g when the temperature of the solution was 70° C. and the stirring was continued for another 2.5 min. The flocculation agent Radiaflot was also added to the solution and more exactly 6.0 g at 25° C. and 4.0 g at 70° C. After another 1.5 min the air flow to the flotation cell was turned on leading to the formation of gas (air) bubbles which rose upwards in the cell. After 5 min of flotation the water pump of the flotation cell was started and after another 5 min the air flow was turned off and the flotation was ended. Samples of the foam formed were taken for manganese analysis.

This analysis was made with the aid of ICP-AES of the type "Thermo Jarrel Ash, Iriak Advantage Instrument". 37% of the added manganese was found in the foam, where the manganese was bonded to the added sequestering agent according to the invention. The concentration of manganese in the foam was about fourteen times higher than the concentration of manganese in the solution in the flotation cell.

Even if the degree of separation of the complex and accordingly also of the sequestering agent comprised in the complex is not optimally high, the result is still sensational since there is no separation at all, i.e. it is zero, with traditional sequestering agents such as EDTA, DTPA and NTA. This is common knowledge for everyone skilled in the art.

It is difficult and time consuming to synthesize these new sequestering agents, that is those according to the invention, in the laboratory, and therefore they have still not been produced in amounts allowing the determination of optimal flotation methods and thereby also optimal degrees of separation.

Since the difference in separability between 0 and 37% is so large there is no doubt about that with the right flotation technique it is possible to separate all or substantially all added sequestering agent.

In order to bring down the amount of sequestering agents needed in the separation tests a new and smaller flotation cell, more suitable for cost-efficient optimization studies was build. This new flotation cell has a volume of approximately 1.6 l, a height of 315 mm and an inner diameter of 80 mm. Compressed air used to form the foam is led through a porous sintered glass filter of diameter 60 mm with a nominal porosity of 10-16 μm ("porosity 4") mounted at the bottom of the flotation cell. At the top of the flotation cell a cylinder of an inner diameter of 30 mm and a height of 415 mm, with an outlet placed at 72 mm from the bottom, is mounted. The outlet is used to collect the foam and thereby the chelate according to the invention. At the top of the latter cylinder an adjustable valve is mounted to be able to better control the foaming and to direct the foam to the outlet.

With this new flotation cell the following laboratory experiments were performed; Examples 3-5.

Example 3

A sequestering agent, 4-dodecyl-3,6,9-tri(carboxymethyl)-3,6,9-triazaundecane diacid, 1 mg of manganese in the form of manganese sulphate (in a molar ratio of 1.2:1=sequestering agent:manganese sulphate) and a flotation agent (N,N-dimethyldodecylamine N-oxide, in a molar ratio of 10:1=flotation agent:sequestering agent) were mixed in 500 ml deionised water. The pH-value of the solution was adjusted to pH 5.5 with 0.1 M sodium hydroxide solution or 0.1 M hydrogen chloride solution. The solution was carefully stirred in 30 min for equilibration. Thereafter the solution was transferred to the earlier described flotation cell. Deionised water (pH adjusted to 5.5) was added to a total volume of 1000 ml. At the beginning 2.5 ml of the solution were taken for determination of the manganese content. Air flow to the flotation cell was turned on leading to the formation of gas (air) bubbles which rose upwards in the cell. Fractions of foam were collected (5-20 g each) until the foam formation decreased to a minimum and the fraction contained mostly water (approximately 30 min). 2.5 ml of each fraction of foam and the residual solution were taken for manganese analysis.

The same experiment as above was also performed with 1 mg of copper in form of copper sulphate. These analyses were made with the aid of ICP-AES of the type "Thermo Jarrel Ash, Iriak Advantage Instrument". About 90% of the added manganese or copper were found in the foam, where the manganese or copper were bonded to the added sequestering agent according to the invention. The concentration of manganese or copper in the foam was about twenty times higher than the concentration of manganese or copper in the solution before the flotation.

Example 4

A sequestering agent, 4-decyl-3,9-di(carboxymethyl)-3,6,9-triazaundecane diacid, 1 mg of manganese in the form of manganese sulphate (in a molar ratio of 1.2:1=sequestering agent:manganese sulphate) and a flotation agent (N,N-dimethyldodecylamine N-oxide, in a molar ratio of 10:1=flotation agent:sequestering agent) were mixed in 500 ml deionised water. The pH-value of the solution was adjusted to pH 5.5 with 0.1 M sodium hydroxide solution or 0.1 M hydrogen chloride solution. The solution was carefully stirred in 30 min for equilibration. Thereafter the solution was transferred to the earlier described flotation cell. Deionised water (pH adjusted to 5.5) was added to a total volume of 1000 ml. At the beginning 2.5 ml of the solution were taken for determination of the manganese content. Air flow to the flotation cell was turned on leading to the formation of gas (air) bubbles which rose upwards in the cell. Fractions of foam were collected (5-20 g each) until the foam formation decreased to a minimum and the fraction contained mostly water (approximately 30 min). 2.5 ml of each fraction of foam and the residual solution were taken for manganese analysis.

These analyses were made with the aid of ICP-AES of the type "Thermo Jarrel Ash, Iriak Advantage Instrument". About 90% of the added manganese was found in the foam, where the manganese was bonded to the added sequestering agent according to the invention. The concentration of manganese in the foam was about twenty times higher than the concentration of manganese in the solution before the flotation.

Example 5

A sequestering agent, 4-decyl-3,6,9-tri(carboxymethyl)-3,6,9-triazaundecane diacid, 1 mg of manganese in the form of manganese sulphate (in a molar ratio of 1.2:1=sequestering agent:manganese sulphate) and a flotation agent (N,N-dimethyldodecylamine N-oxide, in a molar ratio of 10:1=flotation agent:sequestering agent) were mixed in 500 ml deionised water. The pH-value of the solution was adjusted to pH 5.5 with 0.1 M sodium hydroxide solution or 0.1 M hydrogen chloride solution. The solution was carefully stirred in 30 min for equilibration. Thereafter the solution was transferred to the earlier described flotation cell. Deionised water (pH adjusted to 5.5) was added to a total volume of 1000 ml. At the beginning 2.5 ml of the solution were taken for determination of the manganese content. Air flow to the flotation cell was turned on leading to the formation of gas (air) bubbles which rose upwards in the cell. Fractions of foam were collected (5-20 g each) until the foam formation decreased to a minimum and the fraction contained mostly water (approximately 30 min). 2.5 ml of each fraction of foam and the residual solution were taken for manganese analysis.

The same experiment as above was also performed with 1 mg of copper in form of copper sulphate. These analyses were made with the aid of ICP-AES of the type "Thermo Jarrel Ash, Iriak Advantage Instrument". About 80% of the added manganese or copper were found in the foam, where the manganese or copper were bonded to the added sequestering agent according to the invention. The concentration of manganese or copper in the foam was about fifteen times higher than the concentration of manganese or copper in the solution before the flotation.

From the results of the experiments presented in Examples 3-5 it is seen that the recovery of the chelates is dramatically improved compared with what is presented in Example 2. This is mainly due to an optimization of the pH-value of the solution before flotation (pH 5.5 is better than pH 7) and flotation agent (N,N-dimethyldodecylamine N-oxide is better than EKA RF 4283 and Radiaflot).

The invention claimed is:

1. A chemical for chelation of metal ions and separation/recovering of formed chelates, wherein the metal ions are at least bivalent and are contained in water containing and/or water enclosed objects, wherein the chemical corresponds in structure to a following formula

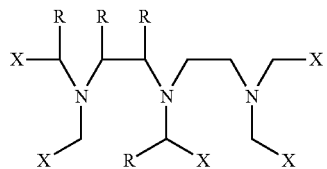

wherein either:
  (1) R in at least one of the positions shown is a straight or branched hydrocarbon chain having 9 to 20 carbon atoms and optionally 1-2 heteroatoms and R is H in the remaining positions and
  X in at least four of the positions shown is —COOH or a salt thereof and wherein when X is —COOH in four of the positions shown, X is H in the remaining position or
  (2) R is H in all four positions shown and X in at least one position is —COOR or —CONHR or —CH₂OR or —COR or —CH₂OCOR or —CH₂OCONHR, wherein R is a straight or branched hydrocarbon chain having 9 to 20 carbon atoms and optionally 1-2 heteroatoms, and
  X in the remaining positions shown is —COOH or a salt thereof.

2. The chemical according to claim 1, wherein R occurs in at least one of the three positions to the left and at the top of the formula.

3. The chemical according to claim 2, wherein R occurs in position 2, counted from the left in the formula.

4. The chemical according to claim 1, wherein the number of carbon atoms in the hydrocarbon chain of R is 10 to 14.

5. The chemical according to claim 1, wherein the number of carbon atoms in the hydrocarbon chain of R is 15 to 20.

6. The chemical according to claim 1, wherein R is H in all four positions shown and X is —CONHR or —CH₂OR or —COR.

7. The chemical according to claim 1, wherein the 1-2 heteroatoms comprise at least one atom selected from the group consisting of sulphur, oxygen and nitrogen.

8. The chemical according to claim 7, wherein R in at least one of the positions shown is a straight or branched hydrocarbon chain having 9 to 20 carbon atoms and contains 1-2 heteroatoms at the point of attachment to the formula.

9. The chemical according to claim 1, wherein the chemical comprises 4-dodecyl-3,6,9-tri(carboxymethyl)-3,6,9-triazaundecane diacid or a salt thereof.

10. A chemical for chelation of metal ions and separation/recovering of formed chelates, wherein the metal ions are at least bivalent and are contained in water containing and/or water enclosed objects, wherein the chemical corresponds in structure to a following formula

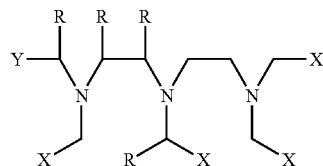

wherein:
  R in at least one of the positions shown is a straight or branched hydrocarbon chain having from 9 to 20 carbon atoms and optionally 1-2 heteroatoms and R is H in the remaining positions,
  X is —COOH or a salt thereof and
  Y is —COOR or —CONHR, or —CH₂OR or —COR or —CH₂OCOR or —CH₂OCONHR, wherein R is a straight or branched hydrocarbon chain having 9 to 20 carbon atoms and optionally 1-2 heteroatoms.

11. The chemical according to claim 10, wherein the chemical comprises 4-decyl-3,6,9-tri(carboxymethyl)-3,6,9-triazaundecanediacid-1-carboxy-11-N-decylamide or a salt thereof.

12. The chemical according to claim 10, wherein the chemical comprises 3,6,9-tri(carboxymethyl)-3,6,9-triazaundecanediacid-1-carboxy-11-N-dodecylamide or a salt thereof.

13. A method for recovering a sequestering agent, which is reacted with metal ions to form a complex, wherein the metal ions are at least bivalent and are contained in a water containing and/or water enclosed object, the method comprising the steps:
  separating the complex formed in a liquid phase from a metal relieved object;
  floating the complex, where gas bubbles flow upwards in the liquid phase together with becoming and/or existing solid substances, including the complex, in the form of a foam to the liquid surface; and
  removing the foam from the liquid surface;
wherein the sequestering agent added to react with the metal ions is a chemical corresponding in structure to a following formula

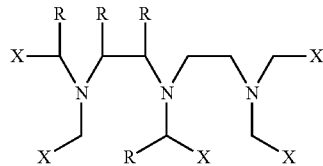

wherein either:
(1) R in at least one of the positions shown is a straight or branched hydrocarbon chain having 9 to 20 carbon atoms and optionally 1-2 heteroatoms and R is H in the remaining positions and X in at least four of the positions shown is —COOH or a salt thereof and wherein when X is —COOH in four of the positions shown, X is H in the remaining position or (2) R is H in all four positions shown and X in at least one position is —COOR or —CONHR or —CH$_2$OR or —COR or —CH$_2$OCOR or —CH$_2$OCONHR, wherein R is a straight or branched hydrocarbon chain having 9 to 20 carbon atoms and optionally 1-2 heteroatoms, and X in the remaining positions shown is —COOH or a salt thereof.

14. The method according to claim 13, wherein the water containing and/or water enclosed object is pulp fibers which are treated with the sequestering agent for recovering the metal ions of interest in the pulp fibers and wherein the method further comprises separating the pulp fibers from the liquid phase containing the formed complexes in subsequent washing using fatty acids and resinous acids released from the pulp fibers to facilitate the formation of said foam.

15. The method according to claim 13, wherein the method further comprises adding a surfactant to the liquid phase to facilitate the formation of said foam, wherein the object does not release fatty acids and/or resinous acids.

16. The method according to claim 13, wherein the recovered foam in original or collapsed form is taken to combustion or dumping.

17. The method according to claim 13, further comprising: adding an acid to the recovered foam to lower the pH-value of the foam to within pH 0-3, wherein protons (H$^+$) take the place of the metal ion in the complex to form an ion exchanged sequestering agent, precipitating resinous acids and fatty acids or a surfactant together with the metal ions in a liquid phase formed by the foam, separating the resinous acids and fatty acids or the surfactant and the metal ions, extracting the ion exchanged sequestering agent with an organic solvent, wherein the ion exchanged sequestering agent is converted to a solvent phase, and contacting the solvent phase containing the ion exchanged sequestering agent with an aqueous phase solution having a pH-value at or close to pH 7, whereby the ion exchanged sequestering agent transfers into an aqueous phase and is capable of being used again to relieve the object from the metal ion.

18. The method according to claim 17, wherein the acid added is a mineral acid or a carbonic acid.

19. The method according to claim 17, wherein the organic solvent is selected from the group consisting of pentane, hexane, heptane, and ethers.

20. The method according to claim 17, wherein the resinous acids and fatty acids or the surfactant and metal ions are led to combustion or dumping.

21. The method according to claim 17, wherein the solvent phase separated from the aqueous phase is used anew for extraction of ion exchanged sequestering agent.

22. The chemical according to claim 1, wherein the chemical is a racemate or a mixture in different proportions or pure enantiomers.

23. The chemical according to claim 10, wherein the chemical is a racemate or a mixture in different proportions or pure enantiomers.

24. The method according to claim 13, wherein the chemical is a racemate or a mixture in different proportions or pure enantiomers.

\* \* \* \* \*